United States Patent

Yamagishi et al.

[11] 4,269,971
[45] May 26, 1981

[54] ANTIBIOTIC TM-531

[75] Inventors: Michio Yamagishi, Tokorozawa; Akira Kawashima, Tokyo; Taku Mizutani, Ageo; Hiroshi Hara, Kitamoto; Kazutoshi Mizoue, Urawa; Sadafumi Omura, Ageo; Haruo Seto, Uenomachi; Noboru Otake, Yokohama, all of Japan

[73] Assignee: Taisho Pharmaceutical Co., Ltd., Tokyo, Japan

[21] Appl. No.: 108,625

[22] Filed: Dec. 31, 1979

[30] Foreign Application Priority Data

Dec. 29, 1978 [JP] Japan .................. 53-14118

[51] Int. Cl.$^3$ .......... A61K 31/71; C07H 7/06
[52] U.S. Cl. .................. 536/17 R; 424/180; 424/181
[58] Field of Search ............ 536/17 R; 424/180, 181

[56] References Cited

U.S. PATENT DOCUMENTS 4,138,481  2/1979  Marlin et al. .................. 536/17 R

OTHER PUBLICATIONS

Hamill et al., "Jour. Antibiotics", vol. 22, pp. 161-164, 1969.
Liu et al., "Jour. Antibiotics", vol. 29, pp. 21-23, 1976.

Primary Examiner—Johnnie R. Brown
Attorney, Agent, or Firm—Sughrue, Rothwell, Mion, Zinn and Macpeak

[57] ABSTRACT

Antibiotic TM-531 having the formula:

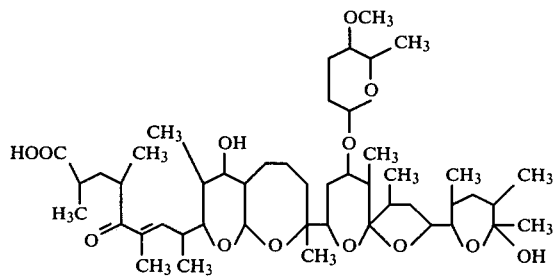

TM-531 is effective against gram-positive bacteria, plant pathogenic microorganisms and protozoa.

1 Claim, 4 Drawing Figures

ANTIBIOTIC TM-531

BACKGROUND OF THE INVENTION

1. Field of the Invention

This invention relates to a novel antibiotic TM-531 having the formula

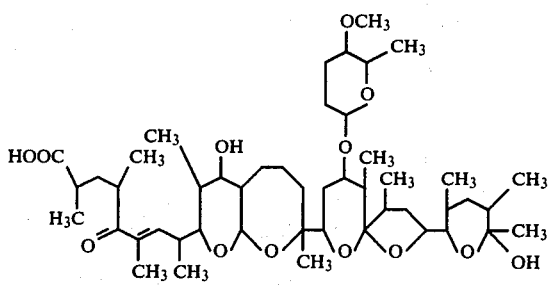

2. Description of the Prior Art

Antibiotic TM-531 of the present invention is a compound belonging to a group of polyether antibiotics which have $\alpha,\beta$-unsaturated ketone group. Some compounds of this group are known and typical examples include antibiotic A-130A as disclosed in J. Antibiotics, 28, 931 (1975), Ro 21-6150 (lenoremycin) as disclosed in J. Antibiotics, 29, 21 (1976) and dianemycin as disclosed in J. Antibiotics, 22, 161 (1969).

However, antibiotic TM-531 is different from any of antibiotic A-130A, Ro 21-6150 and dianemycin in terms of structural formula.

SUMMARY OF THE INVENTION

A primary object of the present invention is to provide a novel antibiotic designated as TM-531 which is effective on gram-positive bacteria, plant pathogenic microorganisms and protozoa.

DETAILED DESCRIPTION OF THE INVENTION

Figure 1:
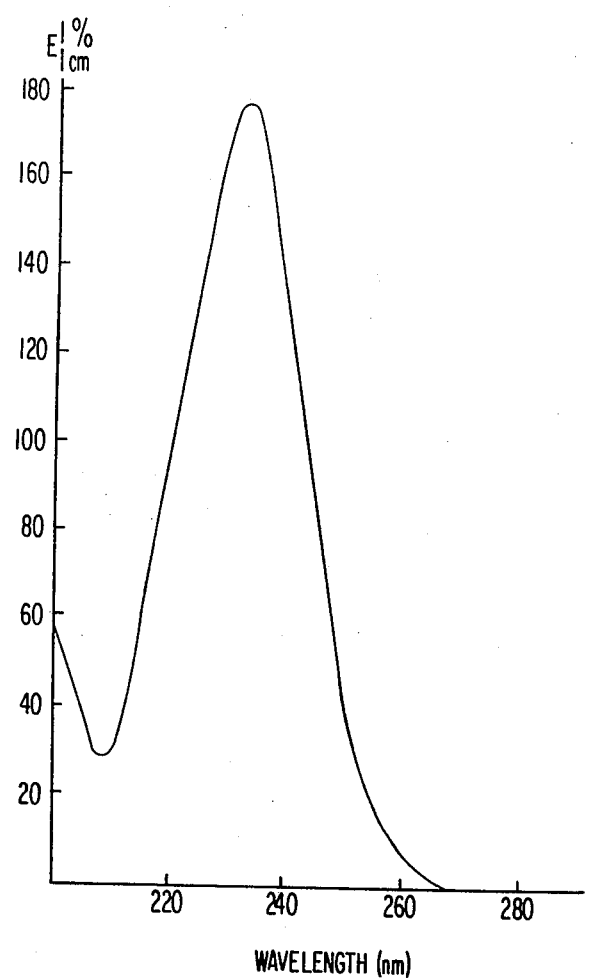
FIG. 1 shows a UV absorption spectrum of antibiotic TM-531 measured in an ethanolic solution.

The present invention relates to a novel antibiotic TM-531 having the formula

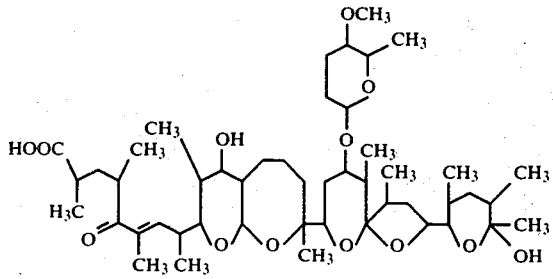

More particularly, the present invention is based on the finding that an antibiotic having a strong growth inhibiting activity against, in particular, gram-positive bacteria, can be accumulated in the culture broth obtained by cultivating TM-531 strain which belongs to the genus Streptomyces and that antibiotic TM-531 can be obtained from the culture broth by extraction and purification.

As a result of investigations on various properties of antibiotic TM-531, the substance was found to be a novel antibiotic distinguished from known antibiotics.

In the present invention, Streptomyces hygroscopicus TM-531 which belongs to the genus Streptomyces is used as an antibiotic TM-531 producing strain. This strain has been newly isolated from a soil sample collected from Omiya-shi, Saitama, Japan and has been deposited under the name of Streptomyces TM-531 at Fermentation Research Institute, Agency of Industrial Science and Technology, Japan, as FERM-P 4737 on Nov. 29, 1978 and at American Type Culture Collection, as ATCC 31590.

The microbiological characteristics of TM-531 strain are as follows.

I. Morphological Characteristics

The aerial mycelium develops well on the oatmeal agar, yeast extract-malt extract agar and glycerin asparagine agar media, etc., and the spore is formed abundantly. The spore-forming hypha is monopodial and the end of aerial mycelia is spiral. Observation by an electron microscope reveals that the surface of spores shows warty. Spore chain at the end of sporophore developed from the aerial mycelia generally contains more than 10 spores, and that the spore is oval or cylindrical in shape having a size of $0.8-1.0\times1.3-1.6\mu$. Flagellospore, sporangium and sclerotium are not observed.

II. Cultural Characteristics

The cultural characteristics of TM-531 strain cultivated on various media at 28° C. for 14 days are shown in Table 1 below.

TABLE 1

| Medium | Growth | Aerial Mycelium | Soluble Pigment | Others |
|---|---|---|---|---|
| Sucrose nitrate agar | Good, wet gray | None | None | |
| Glucose asparagine agar | Slightly poor, pale yellowish white | Almost no development | | |
| Glycerin asparagine agar (I.S.P. Medium No. 5) | Good, pale yellowish white, partially gray | Abundant yellowish white to grayish brown | None | |
| Starch agar (I.S.P. Medium No. 4) | Good, white to gray | Abundant, grayish brown, partially white | None | |
| Tyrosine agar (I.S.P. Medium No. 7) | Fair, yellowish white to grayish white | Fairly abundant pale yellow to grayish brown | Very faint pale brown pigment | |
| Nutrient agar | Slightly poor, wet pale | None | None | |

TABLE 1-continued

| Medium | Growth | Aerial Mycelium | Soluble Pigment | Others |
|---|---|---|---|---|
| | yellowish white | | | |
| Yeast extract-malt extract agar (I.S.P. Medium No. 2) | Fair, yellowish white to gray | Fairly abundant pale yellow to grayish brown | None | |
| Oatmeal agar (I.S.P. Medium No. 3) | Good, white to gray | Fairly abundant grayish brown | None | |
| Peptone yeast extract iron agar (I.S.P. Medium No. 6) | Slightly poor, wet pale yellow | None | None | |
| Glucose Czapek agar | Good, white to yellowish white | Good, white to grayish brown | None | |
| Blood agar | Good, wet gray | None | None | Hemolysis |
| Potato dextrose agar | Fair, pale yellowish white to grayish white | Fairly abundant yellowish white to grayish brown | None | |
| Skim milk | Slight growth along tube wall, white | None | None | No coagulation, strong peptonization |
| Glucose peptone gelatin | Slight growth along tube wall, white | None | None | Weak liquefaction |

III. Physiological Characteristics (1) Temperature Range for the Growth

The strain grows at a temperature in the range of 18° to 45° C. on an oatmeal agar medium. The optimum temperature ranges from 28° to 35° C.

(2) Aerobic or Non-aerobic
   Aerobic (3) Actions on Proteins
   (a) Liquefaction of gelatin: Positive
   (b) Coagulation of skim milk: Negative
   (c) Peptonization of skim milk: Positive
   (d) Liquefaction of Loeffler's coagulated serum: Positive (4) Hydrolysis of Starch: Positive (5) Reduction of Nitrates: Positive (6) Production of Melanoid Pigments: Negative

IV. Utilization of Carbon Sources

The utilization of various carbon sources by TM-531 strain is determined by adding the following carbon source to Pridham and Gottlieb agar medium (I.S.P. Medium No. 9) at 1% concentration and cultivating the strain at 28° C. for 14 days. The results are shown below.

| Carbon Source | Utilizaton |
|---|---|
| L-Arabinose | + |
| D-Xylose | + |
| D-Glucose | + |
| Mannose | + |
| D-Fructose | + |
| L-Rhamnose | + |
| Raffinose | + |
| D-Mannitol | + |
| Galactose | + |
| Maltose | + |
| Starch | + |
| Inulin | + |
| Lactose | ± |
| Sucrose | ± |
| Inositol | ± |
| Trehalose | ± |
| Sorbitol | − |
| Cellulose | − |

The morphological, cultural and physiological properties as well as the utilization of carbon sources of TM-531 strain described above were compared with a wide variety of known strains described in R. E. Buchanan & N. E. Gibbons, "Bergey's Manual of Determinative Bacteriology", 8th ed., 1974; S. A. Waksman's "The Actinomycetes", Vol. 2, 1961 and "The International Streptomyces Project" (I.S.P.), and the following characteristic features were noted.

(1) TM-531 strain forms a spiral of 2 or 3 coils at the end of aerial mycelium.

(2) The color of aerial mycelium developed by TM-531 strain is basically brownish gray, although the color somewhat varies depending upon the type of culture media and the stage of cultivation.

(3) On the media where TM-531 develops abundant aerial mycelium, some wet, dark brown spots are observed partially on the aerial mycelium at the matured stage and thereafter the spots gradually spread over the entire of aerial mycelia.

(4) TM-531 almost does not produce soluble pigments upon cultivation on synthetic media and natural media. These basic and important characteristics are quite consistent with those of Streptomyces hygroscopicus Waksman and Henrici (1948), but TM-531 strain slightly differs from the latter strain in the growth characteristics on the sucrose nitrate agar and nutrient agar media.

From the above features, the present inventors identified that the TM-531 strain belongs to Streptomyces hygroscopicus and designated as Streptomyces hygroscopicus TM-531.

The culture medium used in the production of antibiotic TM-531 of the present invention comprises about 1 to 10% by weight of carbon sources, about 0.1 to 4% by weight of nitrogen sources and about 0.01 to 1% by weight of inorganic components and, if necessary, the medium may contain less than about 1% by weight of defoaming agents. A preferred medium comprises 2 to 6% by weight of carbon sources and 0.5 to 2% by weight of nitrogen sources.

Examples of carbon sources are glucose, maltose, sucrose, starch, glycerin, dextrin, etc., or a mixture thereof.

Examples of nitrogen sources are peptone, beef extract, soybean meal, corn steep liquor, yeast extract, oatmeal, triptone, etc., or a mixture thereof.

Examples of inorganic components are phosphates, sulfates or chlorides of magnesium, iron, zinc or manganese, and the like.

Examples of defoaming agents are Adekanol, silicone and the like.

The cultivation can be advantageously conducted by aerobic culture such as shake culture, aerated submerged culture, and the like, at a pH value of about 5.5 to about 8.0 at a temperature of from about 20° to about 40° C. for a period of about 2 to about 5 days, preferably at pH 6.6 to 7.0 and at 28° to 35° C. for about 3 days.

The isolation of antibiotic TM-531 can be achieved by a conventional procedure for recovering fermentation products from the culture broth. For example, after completion of the cultivation, the culture broth is centrifuged to separate into microbial cells and supernatant. An active substance can then be extracted from the supernatant with a water-insoluble organic solvent such as ethyl acetate, benzene, chloroform and the like. Also, the same active substance as above can be extracted from the microbial cells with an organic solvent such as a lower alcohol, e.g., methanol, ethanol, etc., acetone and the like. The resulting extract is concentrated and the active substance contained in the concentrate is transferred to the same solvent as used in the extraction from the supernatant. The extract thus obtained is combined with the extract of supernatant described above, and the combined extract is concentrated under reduced pressure to obtain a concentrated syrup. The syrup is dissolved in an organic solvent such as benzene, acetone and the like and the solution is subjected to an appropriate combination of usual purification procedures such as silica gel column chromatography, gel filtration on Sephadex LH-20, etc. to obtain active fractions, and from which antibiotic TM-531 can be isolated.

Antibiotic TM-531 has been identified as having the following structural formula by analyses of elementary analysis values, molecular weight, UV absorption spectrum, IR absorption spectrum, $^1$H-NMR spectrum and $^{13}$C-NMR spectrum, and the physico-chemical properties of antibiotic TM-531 are as follows:

(I) Structural Formula

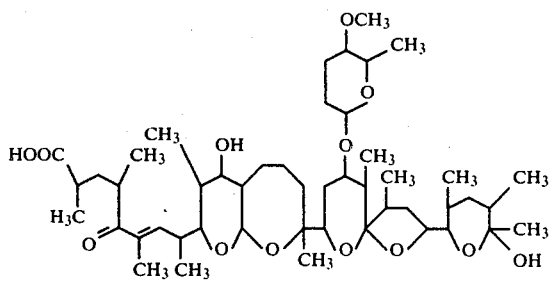

Figure 2:
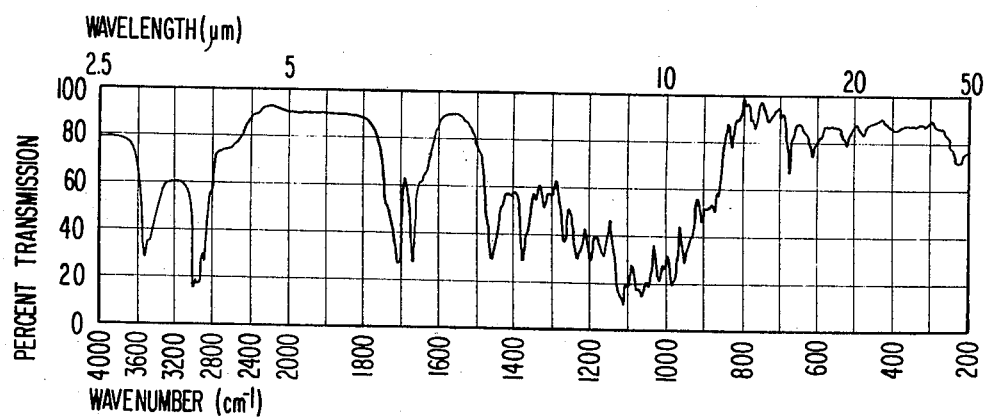
FIG. 2 shows an IR absorption spectrum of antibiotic TM-531 measured by the KBr tablet method.

(II) Physico-chemical Properties (a) Appearance: White Powder
(b) Melting Point: 88°-91° C.
(c) Elementary Analysis: C, 66.40%; H, 9.49%; O, 24.25%
(d) Molecular Weight: 850
(e) $[\alpha]_D^{26}$: +81.2° (C=1, chloroform)
(f) UV Absorption Spectrum: The spectrum determined in ethanol is shown in FIG. 1. $E_1\ _{cm}^{1\%}$ (232 nm)=177.6
(g) IR Absorption Spectrum: The spectrum determined with KBr tablet is shown in FIG. 2 which shows the following characteristic absorption bands.

$\delta(cm^{-1})$=3490, 2960, 2920, 2860, 2810, 1735, 1710, 1667, 1648, 1460, 1376, 1342, 1318, 1262, 1232, 1220, 1200, 1162, 1112, 1095, 1075, 1060, 1046, 1022, 1015, 1000, 982, 950, 938, 930, 908, 890, 874, 864, 830, 810, 790, 775, 760, 738, 700.

Figure 3:
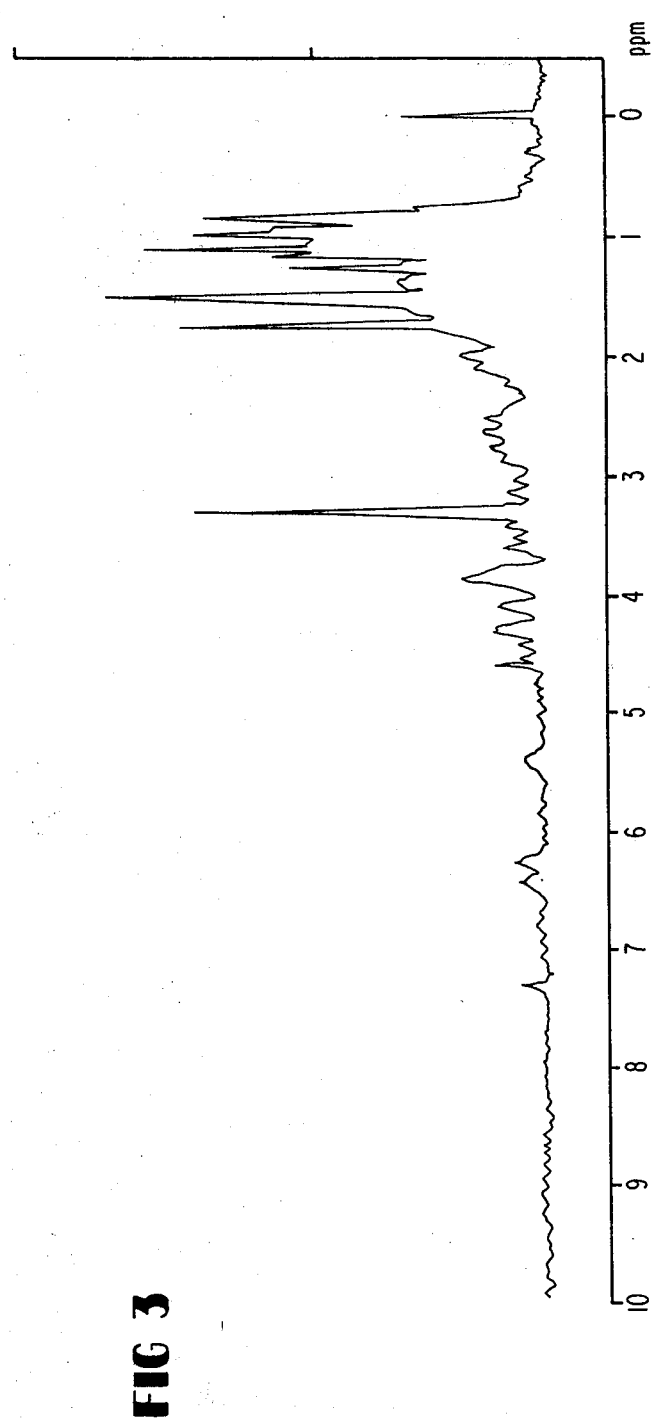
FIG. 3 shows a $^1$H-NMR spectrum of antibiotic TM-531 measured in deuterochloroform (CDCl$_3$) at 60 MHz.
Figure 4:
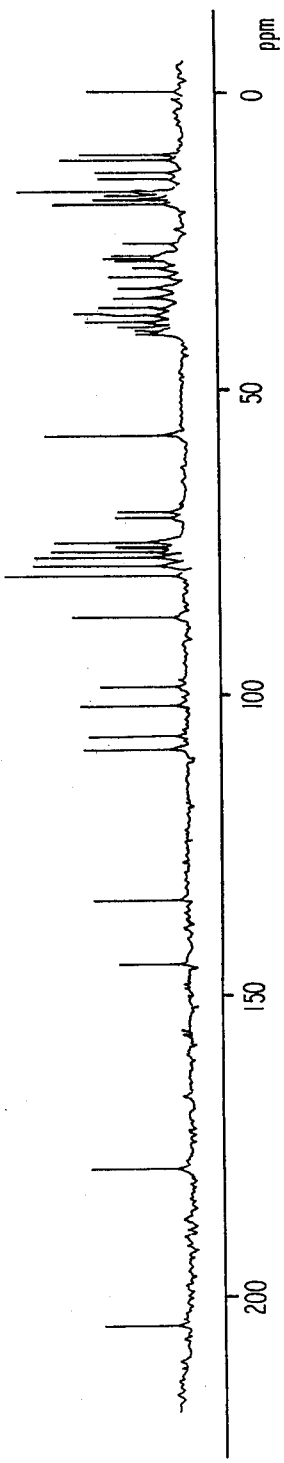
FIG. 4 shows a $^{13}$C-NMR spectrum of antibiotic TM-531 measured in CDCl$_3$ at 25.05 MHz.

(h) Nuclear Magnetic Resonance Spectrum: The $^1$H-NMR spectrum determined in CDCl$_3$ at 60 MHz is shown in FIG. 3 which shows a signal at $\tau$=6.72 (methoxy group). The $^{13}$C-NMR spectrum at 25.05 MHz of antibiotic TM-531 in CDCl$_3$ shows the characteristic resonance at 144.9 and 134.2 ppm which suggest the presence of an olefine group, and at 204.4 ppm which suggests the presence of a ketone group.

(i) Solubility: Antibiotic TM-531 is insoluble in water and soluble in methanol, ethanol, acetone, ethyl acetate, diethyl ether, benzene, chloroform, hexane and petroleum ether.

(j) Color Reaction: Antibiotic TM-531 gives positive color reaction with iodine and potassium permanganate, but negative reaction with ninhydrin and ferric chloride.

(III) Physiological Properties

Antibiotic TM-531 exhibits growth inhibitory activity on gram-positive and plant pathogenic microorganisms, and also is effective on protozoa as hog dysentery, coccidium, toxoplasma, trypanosome, malaria, etc. Antibiotic TM-531 is, however, ineffective on gram-negative bacteria and yeasts.

Antibiotic TM-531 is also effective in improving the feed efficiency when it is incorporated into feeds for poultry, cattle, hogs, etc.

As described above, antibiotic TM-531 is a novel antibiotic which exhibits an excellent growth inhibitory activity against gram-positive bacteria, plant pathogenic microorganisms and protozoa and, therefore, is useful as pharmaceuticals, veterinary medicines and antimicrobial agents for plants. Further, antibiotic TM-531 can be incorporated into feeds to prevent and treat the coccidiosis in domestic animals and poultry as well as to accelerate the growth of domestic animals and poultry.

The present invention is further illustrated by the following Test Examples which show the physiological activity of antibiotic TM-531 and Example which shows the preparation of antibiotic TM-531.

TEST EXAMPLE 1

The antimicrobial activity of antibiotic TM-531 was determined in terms of the minimum inhibitory concentration (MIC) using a heart infusion agar medium for the determination of activity on bacteria and a potato dextrose agar medium for the determination of activity on fungi and yeast. The results obtained are shown in Table 2 below.

TABLE 2

| Antimicrobial Activity of Antibiotic TM-531 | |
|---|---|
| Test Organism | Minimum Inhibitory Concentration (mcg/ml) |
| Staphylococcus aureus FDA 209 P | 1.56 |
| Staphylococcus aureus Smith | 6.25 |
| Staphylococcus aureus TRP-23 | 3.13 |
| Staphylococcus epidermidis TRP-13 | 3.13 |
| Staphylococcus epidermidis TPR-25 | 3.13 |
| Bacillus subtilis ATCC 6633 | 1.56 |
| Bacillus licheniformis | 1.56 |
| Micrococcus luteus NIHJ | 3.13 |
| Corynebacterium xerosis | 1.56 |
| Streptococcus faecalis ATCC 8043 | 6.25 |

TABLE 2-continued

Antimicrobial Activity of Antibiotic TM-531

| Test Organism | Minimum Inhibitory Concentration (mcg/ml) |
|---|---|
| Escherichia coli NIHJ C-2 | >100 |
| Pseudomonas aeruginosa IID 1052 | >100 |
| Proteus vulgaris HX 19 | >100 |
| Aspergillus niger NHL 5088 | >100 |
| Penicillium citrinum IAM 7003 | >100 |
| Trichophyton asteroides | >100 |
| Candida albicans | >100 |
| Saccharomyces cerevisiae | >100 |

TEXT EXAMPLE 2

10 ml of a potato dextrose agar medium was placed in a Petri dish having a diameter of 9 cm, and inoculated with each of the plant pathogenic microorganisms shown in Table 3 below. The medium was incubated at 28° C. for 4 days to grow the organism over the entire surface of the medium and a disk of colony having a diameter of 8 mm was cut from the medium. Separately, 10 ml of the same potato dextrose agar medium containing antibiotic TM-531 at a concentration of 100 mcg/ml was placed and solidified in a Petri dish having a diameter of 9 cm and the above disk of medium was placed at the center of the medium. The resulting medium was then incubated at 28° C. for 7 days and the growth inhibitory activity of antibiotic TM-531 on the plant pathogenic microorganism was evaluated in terms of colony diameter, in comparison with the colony diameter on a control medium, i.e., the same potato dextrose agar medium as used above but containing no antibiotic TM-531. The results obtained are shown in Table 3 below.

TABLE 3

Growth Inhibitory Activity of Antibiotic TM-531 on Plant Pathogenic Microorganisms

| | Colony Diameter (mm) | |
|---|---|---|
| Test Organism | Control Medium | TM-531 Containing Medium |
| Glomerella cingulata | 27.3 | 13.4 |
| Piricularia sasakii | 63.3 | 63.0 |
| Gibberella fujikuroi | 27.6 | 20.2 |
| Botrytis cinerea | 47.7 | 46.7 |
| Helminthosporium sigmoldeum | 22.8 | 15.4 |

TEST EXAMPLE 3

A mice macrophage cultured on a TC-199 medium containing 20% of calf serum was infected with Toxoplasma tachyzoites (hereinafter referred to as "T. tachyzoites") and cultured at 37° C. for about 1 hour. Thereafter, the resulting culture was washed with a phosphate buffer having pH 7.2 to wash out non-infected T. tachyzoites and an ethanol solution of antibiotic TM-531 was added to the medium at an appropriate concentration of antibiotic TM-531. The medium containing the protozoa and antibiotic TM-531 was incubated at 37° C. for 48 hours and then stained with Trypan Blue, and the number of T. tachyzoites per 100 macrophages was counted to determine the antitoxoplasma activity of antibiotic TM-531 as compared with the number of T. tachyzoites per 100 macrophages in the control medium containing no antibiotic TM-531. The results obtained are shown in Table 4 below.

TABLE 4

Antitoxoplasma Activity of Antibiotic TM-531

| | Percent Macrophage infected with T. tachyzoites | |
|---|---|---|
| | T. tachyzoites 1 ~ 5/cell | T. tachyzoites ≧6/cell |
| Control Medium | 30.8 | 22.4 |
| TM-531 Containing Medium (0.1 ppm) | 0 | 0 |

The observation of the above culture medium by an optical microscope showed no toxic sign on macrophage due to the addition of antibiotic TM-531.

TEST EXAMPLE 4

Male chicks (white leghorn species) immediately after hatching were fed with a mixed feed for chicks containing no anti-coccidium agent until the test started. On the 8th day of feeding, health conditions of the test chicks were observed and the body weight was determined thereby dividing the test chicks into three groups, each group comprising 10 chicks and having an equal distribution of body weight. The test group was fed with a mixed feed for chicks containing 0.01% by weight of antibiotic TM-531 and the infected control group and the healthy group were fed with the same mixed feed but containing no antibiotic TM-531. On the 48th hour of feeding, each of chicks of the test group and the infected control group was infected with $9 \times 10^4$ mature oocysts of Eimeria tenella by oral administration. Eight days after infection, body weight increase (%), mortality (%) and O.P.G. [The number of oocysts ($\times 10^4$) present in 1 g of the content of caecum] were determined, and faeces conditions were observed and compared with those of the healthy group to determine the activity of antibiotic TM-531 against Eimeria tenella. The results obtained are shown in Table 5 below.

TABLE 5

Activity of Antibiotic TM-531 against Eimeria tenella

| | Body Weight Increase (%) | Mortality (%) | O.P.G. ($\times 10^4$) | Faeces Conditions |
|---|---|---|---|---|
| TM-531 Administration Group | 105.1 | 0 | 0 | Normal |
| Infected Control Group | 77.0 | 60 | 17.3 | Loose passage 100% Hemafecial 80% |
| Healthy Control Group | 100.0 | 0 | 0 | Normal |

PREPARATION EXAMPLE

A sterilized liquid medium comprising 2% glucose, 2% oatmeal, 0.3% beef extract, 0.3% sodium chloride, 0.25% calcium carbonate, 0.04% ferric sulfate and 0.04% manganese chloride was inoculated with TM-531 strain, and the inoculated strain was aerobically cultivated at 30° C. for 72 hours with stirring to produce a seed culture.

200 l of a sterile medium having the same composition as above charged in a 250 l-fermentation tank was inoculated with 5 l of the seed culture prepared as above and the culture was aerobically cultivated at 30° C. for 72 hours with stirring. After completion of the cultivation, the resulting fermentation broth was centrifuged to separate the broth into supernatant and microbial cells. The supernatant thus obtained was extracted three times with ethyl acetate and the combined extracts were set aside. The microbial cells were extracted twice with 15 l-portions of acetone and the combined acetone extracts were concentrated until acetone was distilled out and further extracted with ethyl acetate. The resulting extract was combined with the above ethyl acetate extracts and the combined extracts were concentrated under reduced pressure to obtain about 112 g of a brown syrup. The whole amount of the syrup was dissolved in 500 ml of benzene and the solution was adsorbed on a silica gel column (Wakogel C-200, a product of Wako Pure Chemical) which had been treated with benzene.

The column was eluted first with benzene and then with benzene-acetone (95:5 by volume) and the eluate was discarded. The column was subsequently eluted with benzene-acetone (90:10 by volume) and the fractions thus obtained were collected and concentrated to dryness under reduced pressure. The resulting crude product was dissolved in acetone. The acetone solution was gel-filtrated on Sephadex LH-20 (a product of Pharmacia Co.) with acetone and the resulting active fraction was concentrated to dryness under reduced pressure to obtain 6 g of a light yellow powder.

Recrystallization of the product from acetone-water (2:1 by volume) yielded 5.2 g of antibiotic TM-531 as needle crystals.

The needle crystals thus obtained appeared to contain water of crystallization and were dissolved in benzene and concentrated to dryness under reduced pressure to obtain a white powder. The following physico-chemical properties were determined with respect to the white powder thus obtained.

Melting Point: 88°–91° C.
Elementary Analysis: C, 66.40%; H, 9.49%; O, 24.25%
Molecular Weight: 850
$[\alpha]_D^{26}$: +81.2° (C=1, chloroform)

What is claimed is:
1. Antibiotic TM-531 having the formula:

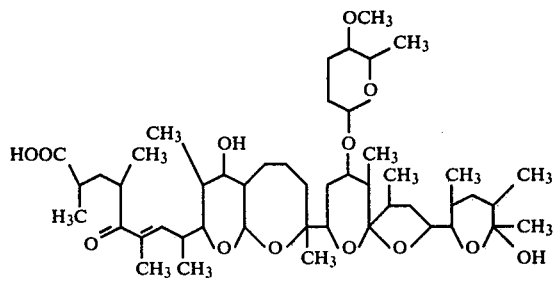

UNITED STATES PATENT OFFICE
CERTIFICATE OF CORRECTION

PATENT NO. : 4,269,971

DATED : May 26, 1981

INVENTOR(S) : Yamagishi et al

It is certified that error appears in the above–identified patent and that said Letters Patent are hereby corrected as shown below:

In the Abstract; in the Specification at column 1, lines 10-20 and lines 55-70 and at column 5, lines 42-54; and in the Claims, at Claim 1, line 2, at each location, change the structural formula to the following:

UNITED STATES PATENT AND TRADEMARK OFFICE
CERTIFICATE OF CORRECTION

PATENT NO. : 4,269,971

DATED : May 26, 1981

INVENTOR(S) : Yamagishi et al

It is certified that error appears in the above-identified patent and that said Letters Patent are hereby corrected as shown below:

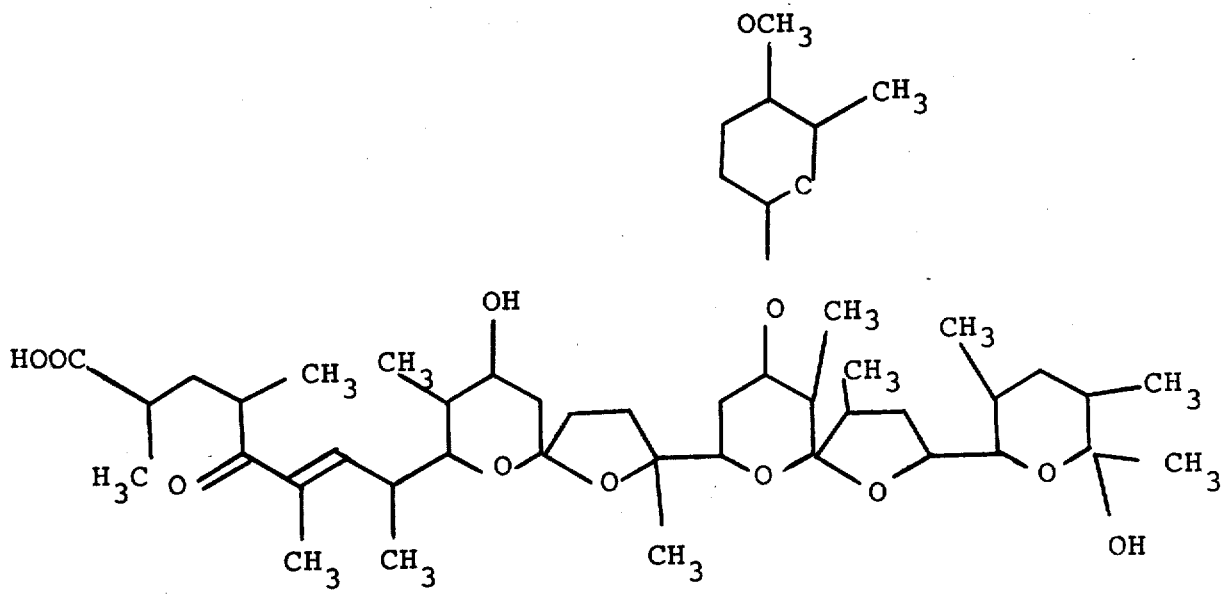

Signed and Sealed this

Second Day of February 1982

[SEAL]

Attest:

Attesting Officer

GERALD J. MOSSINGHOFF

Commissioner of Patents and Trademarks